United States Patent [19]
Vogel et al.

[11] Patent Number: 5,336,087
[45] Date of Patent: Aug. 9, 1994

[54] DEVICE FOR INTRAORAL DETERMINATION OF THE TWO-DIMENSIONAL MANDIBULAR MOVEMENT AND OF THE JAW CLOSING FORCE

[75] Inventors: Andreas Vogel; Rolf Heinze; Klaus-Dieter Wiesinger, all of Leipzig, Fed. Rep. of Germany

[73] Assignee: Transcoject Gesellschaft fur medizinische Gerate mbH & Co. KG, Neumunster, Fed. Rep. of Germany

[21] Appl. No.: 980,782
[22] PCT Filed: Aug. 9, 1991
[86] PCT No.: PCT/EP91/01515
§ 371 Date: Feb. 12, 1993
§ 102(e) Date: Feb. 12, 1993
[87] PCT Pub. No.: WO92/03106
PCT Pub. Date: Mar. 5, 1992

[30] Foreign Application Priority Data
Aug. 14, 1990 [DE] Fed. Rep. of Germany ....... 3434314

[51] Int. Cl.$^5$ .............................................. A61C 19/04
[52] U.S. Cl. .............................................. 433/69
[58] Field of Search ........................... 433/68, 69, 214; 33/513, 514

[56] References Cited

U.S. PATENT DOCUMENTS

| | | | |
|---|---|---|---|
| 2,245,288 | 6/1941 | Moylan | 433/69 |
| 2,252,426 | 8/1941 | Gifford | 433/69 |
| 2,309,270 | 1/1943 | Opotow | 433/68 |
| 3,314,152 | 4/1967 | Frush | 32/19 |
| 4,673,352 | 6/1987 | Hansen | 433/69 |
| 4,788,987 | 12/1988 | Nickel | 433/69 X |
| 4,932,867 | 6/1990 | Ueno | 433/69 |
| 4,964,769 | 10/1990 | Hass | 433/69 X |

FOREIGN PATENT DOCUMENTS

| | | |
|---|---|---|
| 3806028 | 5/1989 | Fed. Rep. of Germany . |
| 3907444 | 8/1990 | Fed. Rep. of Germany . |
| 1306575 | 4/1987 | U.S.S.R. ............... 433/68 |

Primary Examiner—Gene Mancene
Assistant Examiner—Nicholas D. Lucchesi
Attorney, Agent, or Firm—Foley & Lardner

[57] ABSTRACT

A device for intraoral determination of the two-dimensional mandibular movement and of the jaw closing force has a supporting pin carrier arrangement (3) which can be inserted in one jaw (2) and a carrier arrangement (10) which holds a counter plate (11) is mounted in a three-point mounting on a force sensor (14,15) connected to the carrier arrangement (10) and is arranged in a statically determined position.

19 Claims, 2 Drawing Sheets

DEVICE FOR INTRAORAL DETERMINATION OF THE TWO-DIMENSIONAL MANDIBULAR MOVEMENT AND OF THE JAW CLOSING FORCE

The invention relates to a device for the intraoral determination of the two-dimensional mandibular movement and of the jaw closing force.

With a device based on the principle of the so-called supporting pin recording it is possible to determine measured values in a manner which provides an extraorally optical reproduction and/or further evaluation and recording of the measured values by means of electronic data processing which measured values represent an essential condition for a modern stomatological diagnosis and treatment.

The supporting pin technique which was already used extraorally by GYSI in 1908 and converted intraorally by McGrane in 1944 is known. In this connection the movements of the lower jaw in relation to the upper jaw are recorded by means of a recording stylus and a recording plate inserted in the opposite part of the jaw (Freesmeyer et al. "Supporting Pin Recording", in "Dental-Labor" 06/87). In addition a device is known for the intraoral recording of mandibular movements (DD-A-252 123), on which a secure and reproducible anchoring at the teeth is possible by means of spring flanks provided at the carrier system inserted in the jaw. This device has, however, the disadvantage that the manner in which the measurement results are determined does not enable modern methods of recording, evaluating, and filing to be used. The production of the measuring results cannot be monitored and a first evaluation of the measuring results produced intraorally mechanically cannot be made or cannot be made until the device has been removed from the mouth. A reliable division of the curve patterns produced is no longer possible because of multiple overwriting. A statistical and mathematical evaluation of the measuring results in order to improve the diagnostic findings cannot be effected directly but must first be prepared by the two-dimensional taking up of the measurement curve and digitalization. This results in additional costs and above all in delays so that a rapid diagnosis and application of a treatment is not possible.

A device is also known for analysing the articulation movement between upper and lower jaw (DE-A-3 806 028), on which the mechanical recording system is replaced by a contactless recording system. For this purpose radiation sources and receiver arrangements are provided in plates which can be inserted in the upper and lower jaw, from the relative positions of which the articulation movements can be determined. This device, however, because of the small space for expansions in the mouth, requires very special transmitter and receiver components, which with minimum space must have a high directive efficiency. The installation of the device is therefore relatively expensive.

All modified supporting pin techniques which have been known to date are based on the fact that by inserting a central supporting pin between the upper and lower jaw for uncoupling the occlusion, a physiologically correct, individual position of the lower jaw in relation to the upper jaw is obtained, which is reproducible. Research has shown, however, that the force component in the supporting pin axis which is generated at the time of the recording has a great effect on the geometrical behaviour of the mandibular movement so that a reproduction is only possible with the same force conditions.

The object of the invention is to create a device for the intraoral determination of the mandibular movement and of the jaw closing force, which at the same time picks up intraorally the two-dimensional mandibular movement and the expended jaw closing force.

To achieve this object a device is formed in accordance with the invention with a supporting pin carrier arrangement which can be inserted in the jaw and which holds a supporting pin and with a carrier arrangement which can be inserted in the opposite part of the jaw and which is provided with a counter plate in such a way that the counter plate is held at three points on a force sensor connected to the carrier arrangement. For this purpose the tip of the supporting pin is advantageously constructed as a ball which is mounted movably according to the principle of the ball point pen.

With the device according to the invention, as a result of the special mounting of the counter plate on a force sensor and in spite of the limited expansion of the carrier arrangement to be inserted in the jaw, it is possible to effect an exact measurement or determination of the jaw closing force and the mandibular movement as the counter plate is arranged on the force sensor in a defined manner, which determines displacement movements of the counter plate so that the measuring values which are obtained can be supplied for further evaluation and recording without removing the device from the mouth.

The counter plate is preferably mounted at the carrier arrangement in a punctiform manner so that the supporting points lie on the corners of an equilateral triangle.

In a particularly favoured embodiment the force sensor of the device according to the invention is constructed as a three-arm disk with a distance piece aligned in relation to the carrier arrangement. In this way the force sensor is supported at the carrier arrangement through the distance piece and the arms of the disk form transverse beams at the distance piece which are clamped on one side. The counter plate rests on supporting points provided at the free ends of the arms so that a maximum measuring radius and consequently an increased definition and accuracy is achieved of the displacement movements of the counter plate to be measured, whilst the arms hold the counter plate securely in a statically determined position as a result of their central attachment at the distance piece. In this arrangement the force sensor is not affected by forces acting laterally on the counter plate.

When carrying out the measurement conclusions can be drawn from the relationship of the single forces acting on the three supporting points, i.e. preferably on the free ends of the three arms of the force sensor as to the position of the tip of the supporting pin on the counter plate and from the sum of the measured values as to the jaw closing force. In this way both the position of the supporting pin and the active total force can be determined simultaneously with the device according to the invention. Changes can be followed on a time basis so that several movement paths of the supporting pin can be separated from each other and also evaluated separately. By these means basically sound diagnostic findings are obtained and as comparable findings can also be obtained through the position-force information on the geometry of the set of teeth (change in accordance with the jaw closing force), the device according to the invention is particularly well suited to follow the effects of the treatments which are used. The device is also easy to handle and electronically detected measured values can be processed and stored in computers.

In an embodiment of the device according to the invention with a force sensor in the form of a three-arm disk, extension sensors can be disposed on the arms of the disk, which are arranged between the distance piece and the supports provided in each case at the free end of the arms. The extension sensors can be resistance strain gauges and the signals output by them can be fed to an evaluation circuit via cable connections.

Another means of determining the distortions of the arms of the disk-shaped force sensor consists of disposing in the carrier arrangement below the arms approximation sensors, respectively such as inductive sensors, which for example can be located on a printed circuit board connected to the carrier arrangement and the output signals of which can be fed to an evaluation circuit.

The invention will be explained in greater detail below on the basis of the schematically illustrated examples of embodiments.

Figure 1:
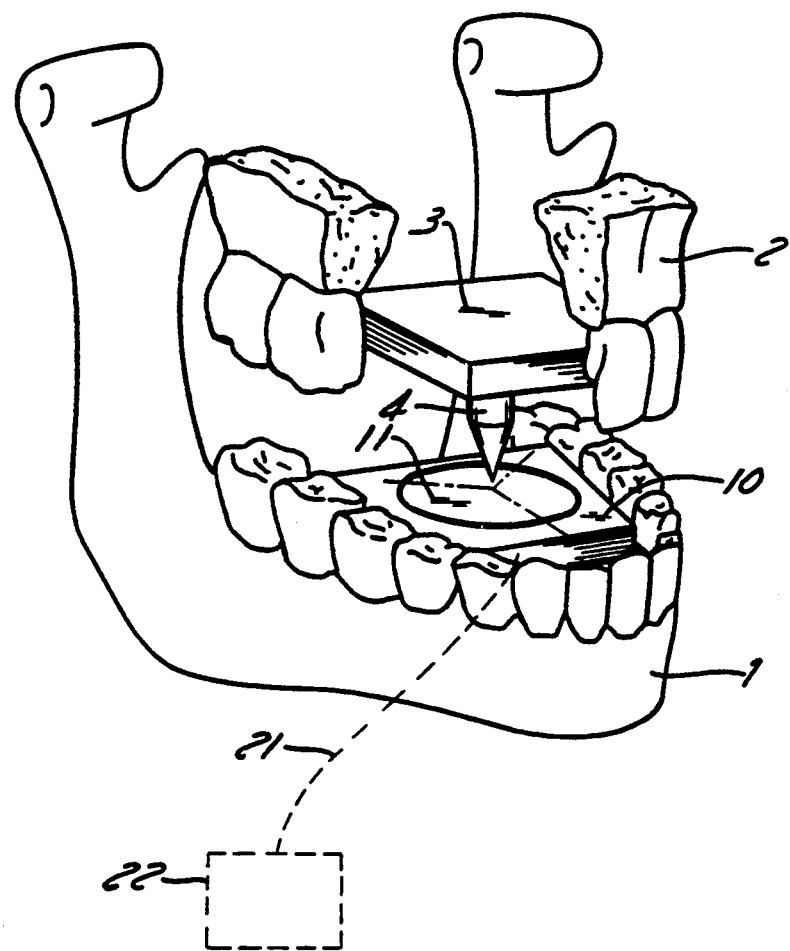
FIG. 1 shows a perspective view of an upper jaw with an inserted supporting pin carrier arrangement and a lower jaw with an inserted carrier arrangement.

A platelike supporting pin carrier arrangement 3 is inserted into the upper jaw 2 of a schematically illustrated set of teeth which is partially shown in FIG. 1 and to the side of this arrangement 3 which is facing the lower jaw 1, there is attached a supporting pin 4, wherein the supporting pin carrier arrangement 3 and the supporting pin 4 are made for example of stainless steel. A platelike carrier arrangement 10, which is made for example of stainless steel, is inserted into the lower jaw 1, and is provided with a central recess which is closed by a counter plate 11 made for example of stainless steel, between which counter plate 11 and the carrier arrangement 10 an elastic ring seal 12 (FIGS. 2 and 3) is located. In order to reduce the friction forces acting in the plane of the counter-plate 11 with the contact of the tip of the supporting pin 4 and the upper surface of the counter plate 11 as a result of the movement of the supporting pin 4 thereon, the tip of the supporting pin 4 can be provided in the same way as a ball-point pen with a movably mounted ball which is not shown.

A force sensor is seated in the recess of the carrier arrangement 10, which force sensor has the shape of a three-arm disk with a central hub-shaped center piece 14 and which has arms 15 which extend from this radially outwards. The lower end surface in FIG. 3 of the hub-shaped center piece 14 is supported on the base of the recess of the carrier arrangement 10 and is non-movably secured in the carrier arrangement 10 by means of a screw 20 which extends through this base.

Figure 2:
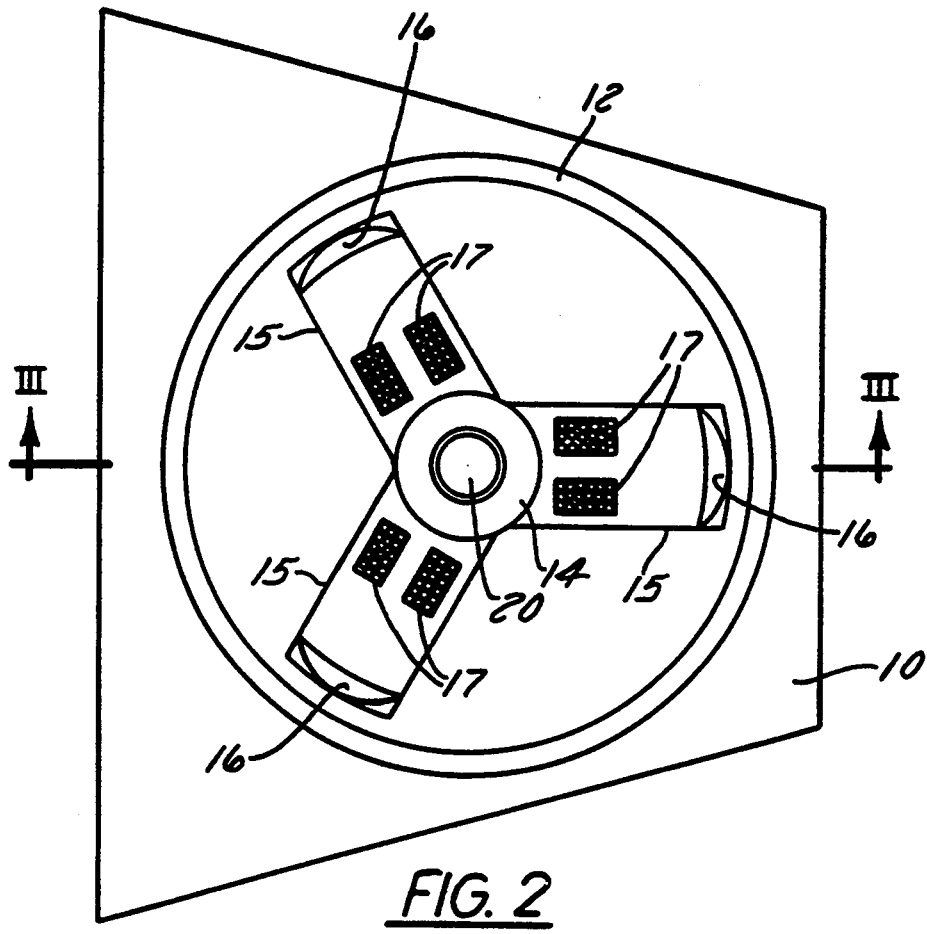
FIG. 2 shows a top view on to the carrier arrangement of FIG. 1, on which the counter plate has been omitted for the sake of clarity.

Raised supporting points 16 for the punctiform mounting and supporting of the counter plate 11 are formed on the free ends of the arms 15 so that, as can be seen particularly in FIG. 2, the three supporting points 16 lie on the corners of an equilateral triangle. It should be noted that downward directed limit protrusions are located at the side of the free ends of the arms 15 shown in FIG. 3 which is facing away from the supporting points 16 and that in normal operation these limit protrusions lie above the base of the recess of the carrier arrangement 10. However with an unacceptably large distortion of the arms 15 these limit protrusions engage the base of the carrier arrangement 10 to provide support and thus prevent the force sensor from being damaged.

Resistance strain gauges 17 are secured to the arms 15 which to an extent are elastically deformable between the hub-shaped center piece 14 and the supporting points 16 and these resistance strain gauges 17 are connected via a cable connection 21 shown schematically in FIG. 1 to an evaluation, indicating and/or recording arrangement 22 which is also shown schematically in FIG. 1.

To determine the mandibular movement and the jaw closing force of a patient the supporting pin arrangement 3 is inserted into the upper jaw 2 and the carrier arrangement 10 is inserted into the lower jaw 1 of the patient. For this purpose the sides of the supporting pin carrier arrangement 3 and carrier arrangement 10 are constructed for example in accordance with DD-A-252 123. If the tip of the supporting pin 4 in this inserted condition is located over the centre of the force sensor 14, 15, i.e. on the centre axis of the screw 20, when the teeth are bit together all three arms 15 of the force sensor are elastically deformed in equal measure with the displacement of their free ends in the direction of the base of the recess in the carrier arrangement 10. The resistance strain gauges 17 which are equally loaded in this case output therefore electrical signals of equal amplitude, which is a measure of the jaw closing force. If the tip of the supporting pin 4 is displaced as a result of the movement of the lower jaw, the arms 15 and thus the resistance strain gauges 17 are deformed variably in accordance with the direction and extent of the displacement. The resistance strain gauges 17 will then output signals with varying amplitudes. The position of the tip of the supporting pin 4 can easily be determined on the counter plate 11 from these signals. The active jaw closing force is determined from the sum of the amplitudes of the electrical signals related to the point of application of the pressure. By picking up the amplitudes of the electrical signals over the period the two-dimensional mandibular movement in relation to the upper jaw can be represented and examined and the force of biting the teeth together which is active at the same time can also be determined.

With the aid of the device according to the invention it is possible for the doctor with repeated measurements and by giving instructions to the patient to influence his jaw closing force in the desired manner so as to determine the movement of the lower jaw which then occurs.

Figure 3:
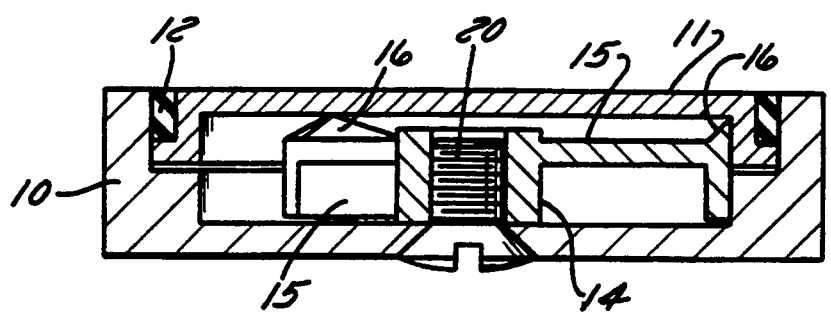
FIG. 3 shows a section along the line II—III of FIG. 2 with the counter plate which was not shown in FIG. 2.
Figure 4:
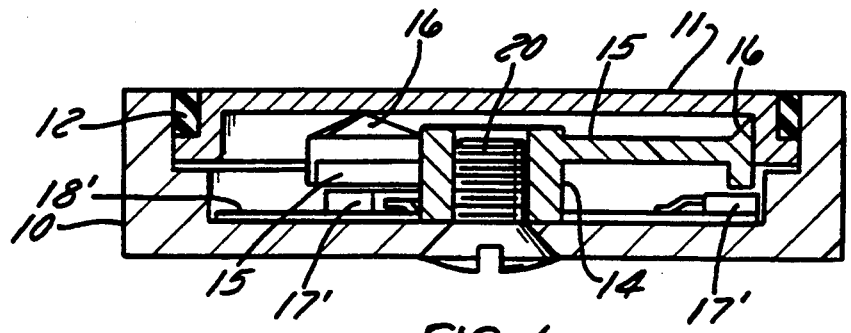
FIG. 4 shows in a similar view to that of FIG. 3, a modified force sensor.

In the embodiment according to FIG. 4 the same parts as in the embodiment according to FIGS. 1 to 3 are identified with the same reference numerals and they will not be described again.

By way of deviation from the embodiment according to FIGS. 1 to 3 no resistance strain gauges for determining the elastic distortions of the arms 15 are provided on the arms 15 of the force sensor, but a printed circuit board 18' is attached to the base of the recess of the carrier arrangement 10 and on this printed circuit board 18' inductive proximity sensors 17' are located below the protrusions formed at the free ends of the arms 15, the output signals of which sensors vary in accordance with the distance of the indicated protrusions of the arms 15 from the corresponding proximity sensor 17′, wherein these output signals can be transmitted outwards in the same manner as has been mentioned in connection with the embodiment according to FIGS. 1 to 3.

Otherwise the mode of operation of the embodiment according to FIG. 4 corresponds to that of the embodiment according to FIGS. 1 to 3.

The device according to the invention has numerous possible applications. As is well known a central problem in dentistry is to make it possible from the therapeutic point of view to find the correct arrangement of the lower jaw in relation to the upper jaw, i.e. the determining of a physiologically correct "jaw relationship". With the aid of the device according to the invention a correct position can be determined and defined in a simple manner and with a high degree of certainty and used for subsequent dentistry operations including the making of bridges or sets of dentures. In addition with the device according to the invention a dysfunctional behaviour in the oral-facial system, as caused by illnesses can also be recorded, so that investigations can be carried out over longer periods.

We claim:

1. A device for intraoral determination of the two-dimensional mandibular movement and of jaw closing force, comprising:
   - a first carrier configured for insertion into a first jaw;
   - a supporting pin protruding from the first carrier;
   - a second carrier which can be inserted in a second jaw, the second jaw being opposite the first jaw;
   - a counter plate disposed on the second carrier;
   - a force sensor disposed on the second carrier, which force sensor supports the counter plate at three points in spaced locations and separately measures force exerted against the counter plate at the three points;
   - whereby two-dimensional mandibular movement and jaw closing force can be determined by measuring force exerted by a tip of the pin against the counter plate at each of the three points.

2. The device of claim 1, further comprising a device for recording, evaluating and/or displaying forces measured by the force sensor, and means for transmitting measured force values from the force sensor to the recording, evaluating and/or displaying device.

3. The device of claim 2, wherein the three points on the force sensor are of punctiform construction and are located on the corners of an imaginary equilateral triangle.

4. The device of claim 1, wherein the force sensor includes a center portion with three lateral arms, each arm forming one of the three points.

5. The device of claim 4, wherein a support protrusion for the counter plate is provided proximate an end of each of the three arms distal from the center portion.

6. The device of claim 5, wherein the center portion comprises a hub, and the arm extend radially from the hub.

7. The device of claim 6, wherein the three points on the force sensor are of punctiform construction and are located on the corners of an equilateral triangle.

8. The device of claim 7, further comprising means for securing the hub of the force sensor to the second carrier.

9. The device of claim 8, wherein the first carrier is configured for insertion into an upper jaw as the first jaw, the second carrier is configured for insertion into a lower jaw as the second jaw, the pin extends downwardly from the center of the first carrier, the counter plate and force sensor are disposed in a recess on an upper surface of the second carrier with the force sensor concealed beneath the counter plate, and a seal is interposed in a space around the outer periphery of the counter plate between the counter plate and the second carrier.

10. The device of claim 1, wherein the first carrier is configured for insertion into an upper jaw as the first jaw, the second carrier is configured for insertion into a lower jaw as the second jaw, the pin extends downwardly from the center of the first carrier, the counter plate and force sensor are disposed in a recess on an upper surface of the second carrier with the force sensor concealed beneath the counter plate, and a seal is interposed in a space around the outer periphery of the counter plate between the counter plate and the second carrier.

11. The device of claim 1, wherein the pin includes a tip comprising a movably mounted ball.

12. The device of claim 1, further comprising means for protecting the force sensor from damage due to excess force applied to the counter plate.

13. The device for intraoral determination of the two-dimensional mandibular movement and of jaw closing force, comprising:
   - a first carrier configured for insertion into a first jaw;
   - a supporting pin protruding from the first carrier;
   - a second carrier which can be inserted in a second jaw, the second jaw being opposite the first jaw;
   - a counter plate disposed on the second carrier;
   - a force sensor disposed on the second carrier, which force sensor has a center portion with three lateral arms, each arm forming one of three points which support the counter plate at spaced locations, and each arm having an extension sensor attached thereto, which extension sensors separately measure force exerted against the counter plate at the three points;
   - a device for recording, evaluating and/or displaying forces measured by the force sensor, and means for transmitting measured force values from the force sensor to the recording, evaluating and/or displaying device;
   - whereby two-dimensional mandibular movement and jaw closing force can be determined by measuring force exerted by a tip of the pin against the counter plate at each of the three points.

14. The device of claim 13, wherein the extension sensors comprise resistance strain gauges.

15. The device of claim 13, further comprising means for attaching the center portion of the force sensor to the second carrier at a location spaced from the arms.

16. The device of claim 15, wherein:
   - the first carrier is configured for insertion into an upper jaw as the first jaw;
   - the second carrier is configured for insertion into a lower jaw as the second jaw;
   - the pin extends from the center of an underside of the first carrier;
   - the counter plate and force sensor are disposed in a recess on an upper surface of the second carrier with the force sensor concealed beneath the counter plate, and a seal is interposed in a space around the outer periphery of the counter plate between the counter plate and the second carrier; and the center portion of the force sensor comprises a hub, the arms extend radially from the hub, and the three points on the force sensor are of punctiform construction and are located on the corners of an imaginary equilateral triangle.

17. A device for intraoral determination of the two-dimensional mandibular movement and of jaw closing force, comprising:

a first carrier configured for insertion into a first jaw;

a supporting pin protruding from the first carrier;

a second carrier which can be inserted in a second jaw, the second jaw being opposite the first jaw;

a counter plate disposed on the second carrier;

a force sensor disposed on the second carrier, which force sensor has a center portion with three lateral arms, each arm forming one of three points which support the counter plate at spaced locations, and further includes three proximity sensors disposed beneath each arm at each of the three points, which proximity sensors separately measure deflection of each arm due to force exerted against the counter plate at the three points; and a device for recording, evaluating and/or displaying forces measured by the force sensor, and means for transmitting measured force values from the force sensor to the recording, evaluating and/or displaying device;

whereby two-dimensional mandibular movement and jaw closing force can be determined by measuring force exerted by a tip of the pin against the counter plate at each of the three points.

18. The device of claim 17, wherein the proximity sensors are inductive sensors fixed on a printed circuit board attached to the second carrier.

19. The device of claim 17, wherein:

the first carrier is configured for insertion into an upper jaw as the first carrier;

the second carrier is configured for insertion into a lower jaw as the second jaw;

the pin extends from the center of an underside of the first carrier;

the counter plate and force sensor are disposed in a recess on an upper surface of the second carrier with the force sensor concealed beneath the counter plate, and a seal is interposed in a space around the outer periphery of the counter plate between the counter plate and the second carrier; and the center portion of the force sensor comprises a hub, the arms extend radially from the hub, and the three points on the force sensor are of punctiform construction and are located on the corners of an imaginary equilateral triangle.

* * * * *